(12) United States Patent
Chiba et al.

(10) Patent No.: US 6,670,309 B2
(45) Date of Patent: Dec. 30, 2003

(54) METHOD AND APPARATUS FOR PREPARING FLUORINE-BASED SOLVENT

(75) Inventors: Hiroshi Chiba, Kawasaki (JP); Keiji Watanabe, Kawasaki (JP); Eishin Yamakawa, Higashine (JP); Takeshi Tokairin, Higashine (JP)

(73) Assignee: Fujitsu Limited, Kawasaki (JP)

( * ) Notice: Subject to any disclaimer, the term of this patent is extended or adjusted under 35 U.S.C. 154(b) by 271 days.

(21) Appl. No.: 09/795,424

(22) Filed: Feb. 28, 2001

(65) Prior Publication Data

US 2002/0035302 A1 Mar. 21, 2002

(30) Foreign Application Priority Data

Aug. 1, 2000 (JP) ........................................ 2000-233478

(51) Int. Cl.[7] ............................................ C10M 175/00
(52) U.S. Cl. ........................ 508/111; 208/18; 208/180; 210/661
(58) Field of Search ........................... 508/111; 208/18, 208/180; 210/661

(56) References Cited

U.S. PATENT DOCUMENTS

| 4,045,330 A | * | 8/1977 | Avrillon et al. | ............. | 208/180 |
|---|---|---|---|---|---|
| 4,597,882 A | * | 7/1986 | Nishimura et al. | ........... | 508/111 |
| 4,996,368 A | * | 2/1991 | Gries | ........................ | 568/601 |
| 5,466,364 A | * | 11/1995 | Kaul et al. | ................... | 208/307 |
| 5,789,534 A | * | 8/1998 | Koike et al. | ................. | 528/407 |
| 5,942,121 A | * | 8/1999 | Pantich | ........................ | 210/664 |
| 6,024,880 A | * | 2/2000 | Ciora, Jr. et al. | ............ | 210/653 |
| 6,111,162 A | * | 8/2000 | Rossini et al. | ............... | 585/824 |

FOREIGN PATENT DOCUMENTS

| JP | 5-20673 | 1/1993 |
|---|---|---|
| JP | 5-135350 | 6/1993 |
| JP | 5-140573 | 6/1993 |
| JP | 8-22617 | 1/1996 |
| JP | 10-53781 | 2/1998 |
| JP | 10-316598 | 12/1998 |
| JP | 10326408 | 12/1998 |
| JP | 11-14204 | 1/1999 |
| JP | 11-199882 | 7/1999 |

* cited by examiner

Primary Examiner—Jacqueline V. Howard
(74) Attorney, Agent, or Firm—Greer, Burns & Crain, Ltd.

(57) ABSTRACT

In preparing a purified fluorine-based solvent from a fluorine-based solution comprising a lubricant based on a fluororesin having an organic terminal group and a fluorocarbon-based solvent, impurities including ionic pollutants contained in the fluorine-based solution or the lubricant are selectively removed by an adsorption process. The preparation apparatus of a purified fluorine-based solvent is also disclosed.

9 Claims, 2 Drawing Sheets

METHOD AND APPARATUS FOR PREPARING FLUORINE-BASED SOLVENT

BACKGROUND OF THE INVENTION

1. Field of the Invention

The present invention relates to a method and an apparatus for preparing a fluorine-based solvent and, more specifically, the present invention relates to a method and an apparatus for preparing a purified fluorine-based solvent useful for the production of various functional elements having on the surface thereof a lubricant layer, and also relates to a lubricant composition and a cleaning agent composition. The lubricant composition of the present invention can be advantageously applied to a magnetic recording layer of a magnetic disk (magnetic recording medium) for use in a hard disk device or the like of computers and to a carbon protective coating for protecting a magnetic head. The term "functional element" used herein means an element designed particularly for a magnetic disk device, such as magnetic disk and magnetic head, or any elements having a lubricant layer capable of exhibiting a certain function.

2. Description of the Related Art

In the field of information processing devices such as computers, a magnetic disk device is widely used as an outer memory unit. When a magnetic disk device is used, the recording or reading of information on a magnetic disk can be performed by moving a magnetic head over the magnetic disk. To cope with recent requirements (for example, recording and reading with high density, high sensitivity and high speed), various improvements have been made on the structure or material of the magnetic disk.

With the progress of high density recording on a magnetic disk, pollution on the disk surface causes a serious problem. More specifically, if a pollutant adheres to the disk surface, the pollutant is scattered due to rotation of the disk during the operation of the magnetic disk device, thereby causing troubles such as corrosion of the magnetic head. Various causes are considered to bring about the adhesion of pollutants, but a lubricant layer formed on the surface of the magnetic disk to attain lubrication seems to be mostly responsible. For forming the lubricant layer, a lubricant composition, obtained by dissolving, for example, a fluororesin-based lubricant in a fluorine-based solvent, is coated on the disk surface and in the preparation or coating step of this composition, trace amounts of pollutants (ionic organic materials in many cases) are incorporated into the composition from the surrounding environment. In order to solve this problem brought about by the polluted lubricant composition, the lubricant composition has been heretofore regularly inspected regarding the amount of ionic organic materials contained therein by ion chromatography and exchanged for a new lubricant composition when the amount of organic materials exceeds a previously determined standard level (upper limit). However, it is very cumbersome and costly to regularly inspect the composition and frequently exchange the used composition with a new and fresh composition. Furthermore, since the fluorine-based solvent is a very expensive chemical, the cost of the treatment is very high.

In recent years, because fluorine-based solvents are widely used in various fields, there is a movement to refining the used lubricant composition and recycling the separated fluorine-based solvent so as to reduce the cost or prevent environmental pollution. However, this purification step is disadvantageous in view of energy savings because the purification must be performed by a distillation operation which requires continuous feeding of the vaporization heat from the beginning to the end of the operation and, also, the cost necessary for the operation of the distillation apparatus increases. As a matter of more importance, this purification step cannot attain complete removal of ionic organic materials contained as a pollutant in the fluorine-based solvent and undesirable residues of the organic materials generally remain in an amount of about 60 ng/ml.

Recently, an operation of coating a lubricant on a disk surface and then rinsing the disk surface with a fluorine-based solvent to wash out the extra lubricant and thereby increase the frictional properties of the magnetic disk is often performed. In this case, the fluorine-based solvent is repeatedly used as a cleaning solution and exchanged for a fresh fluorine-based solvent when the solution is outstandingly soiled. However, according to this cleaning method, as the number of repetitions of using the fluorine-based solvent increases, the amount of pollutants (e.g., lubricant and ionic organic materials) in the solvent also increases, therefore, there arises a problem that the lubricant washed out again adheres to the disk surface and thus the resulting lubricant layer shows a varied distribution in thickness. This problem may be solved by recycling the fluorine-based solvent through distillation, however, this method has the problem described above.

SUMMARY OF THE INVENTION

The object of the present invention is to solve the above-described prior art problems and provide a method and an apparatus for preparing a fluorine-based solvent useful in providing a lubricant composition which is advantageously used in the formation of a lubricant layer on the surface of a functional element such as magnetic recording medium, contains only in a negligible amount of pollutants capable of adversely affecting on the surrounding environment, is inexpensive, and can be easily recycled.

These objects and other objects of the present invention will be easily understood from the following detailed description of the preferred embodiments of the present invention.

The present inventor has found that for removing a trace amount of impurities (ionic organic materials) contained in a fluorine-based solvent and impurities such as residual lubricant from the fluorine-based solvent, it is very effective to introduce and pass the fluorine-based solvent into and through an appropriate adsorbent and allow the adsorbent to selectively trap only impurities.

In one aspect thereof, the present invention resides in a method for preparing a purified fluorine-based solvent from a fluorine-based solution comprising a lubricant based on a fluororesin having an organic group at the terminal of the resin structure and a fluorocarbon-based solvent, comprising an adsorption step of selectively removing impurities including ionic pollutants contained in the fluorine-based solution and the lubricant, by an adsorption process.

In another aspect thereof, the present invention resides in an apparatus for preparing the purified fluorine-based solvent, as mentioned above, comprising an adsorbing station filled with an adsorbent capable of trapping impurities including ionic pollutants contained in the fluorine-based solution and the lubricant, disposed on the way of passage of the fluorine-based solution.

DESCRIPTION OF THE PREFERRED EMBODIMENTS

Before describing the preferred embodiments thereof, the present invention will be described with regard to the function and mechanism of the present invention.

According to the present invention, while taking into consideration of the fact that the fluorine-based solvent has low polarity, a trace amount of foreign matter such as impurities (for example ionic pollutants and residual lubricants), contained in a fluorine-based solvent, particularly in a fluorocarbon-based solvent, are effectively trapped by an adsorbent due to an interaction between trace impurities and the adsorbent. The present inventor assumes that impurities are trapped by the adsorbent in such a mechanism that the polarity of trace impurities is concealed in a normal solvent due to the polarity of the solvent itself but appears in a fluorine-based solvent having low polarity and, as a result, the impurities, even in a trace amount, are completely trapped by the adsorbent due to Coulomb interaction. As such, trace impurities can be trapped, therefore, a high-purity fluorine-based solvent can be recovered effectively, easily and inexpensively from the used fluorine-based solution which must be treated as a waste solution in conventional techniques, for example, a fluorine-based solution containing a lubricant, which is used in the formation of a lubricant layer in the field of production of magnetic recording mediums.

Incidentally, recycling of a fluorine-based solution containing a lubricant is being studied also in conventional techniques, however, the target of the recycling is the recovery and purification of the lubricant. For example, Japanese Unexamined Patent Publication (Kokai) No. 5-20673 discloses a technique of purifying a perfluoropolyether-based lubricant (liquid lubricant) for use in a magnetic recording medium by gel permeation chromatography (GPC method). More specifically, perfluoropolyether is separated through a chromatographic process, according to the molecular weight, using an interaction between the perfluoropolyether and polystyrene filled in the chromatograph column, thereby removing low molecular weight components and impurity components which give rise to unstable quality. However, this method cannot provide an operation effect equal to that obtained by the adsorbent used in the present invention, because the perfluoropolyether-based lubricant and the fluorine-based solvent are different in the chemical structure and also, in the case of purifying the lubricant by the GPC method, the lubricant or the like trapped in the column dissolves out along the prolongation of the elution time and thus, the time control and operation become extremely cumbersome.

Also for the purification of a perfluoropolyether-based lubricant, Japanese Unexamined Patent Publication (Kokai) No. 10-53781 discloses a method of purifying perfluoropolyether to a high purity by column chromatography using silica gel or alumina as a filling agent of the column. However, in this method, silica gel or alumina is used only for the purpose of purification as commonly used in this technical field and not for adsorbing, in other words, for trapping, perfluoropolyether. Although the purification is attained by the repetition of adsorption and desorption, the present inventor has found that the desorption of perfluoropolyether hardly occurs under certain conditions and, based on this principle, the present invention of selectively recovering a high-purity fluorine-based solvent from a fluorine-based solution containing a used lubricant has been accomplished.

Again returning to the function of the present invention, the excellent recycling method of the present invention can attain high purification of a fluorine-based solution containing a lubricant used for forming a lubricant layer and also high purification of a fluorine-based solvent used therein, therefore, the present invention not only contributes to the cost reduction and the environmental conservation but also is useful for preventing pollution or breakage of a magnetic disk device. The lubrication treatment of a magnetic disk contains a rinsing step of washing out a lubricant coated on the disk surface with a fluorine-based solvent and in the present invention, since a small amount of fluorine-based solvent can be used while recycling, a fresh and high-purity fluorine-based solvent can be always continuously fed. Unlike conventional techniques, the fluorine-based solvent need not be consumed in a large amount and therefore, reductions in the cost and in the environment load can be attained.

The purified fluorine-based solvent of the present invention can be prepared by using a fluorine-based solution containing a fluororesin-based lubricant having an organic group at the terminal of the resin structure and a fluorocarbon-based solvent, as a starting material, followed by purifying the fluorine-based solution. The fluorine-based solution as a starting material is not particularly limited, however, a used lubricating solution recovered after the application to the surface of a functional element so as to impart lubrication is preferred. The fluorine-based solution is usually a fluorine-based solution containing a lubricant used for forming a lubricant layer in the production of a functional element (as defined above, the functional element means an element having a lubricant layer, such as a magnetic disk and a magnetic head), and contains impurities such as ionic pollutant and lubricant in an amount large enough to require removal. The ionic pollutants are intermixed as impurities derived from the preparation apparatus, for example, in the stage of preparing a lubricant or a fluorine-based solution. Examples thereof include halogens such as fluorine, bromine and chlorine, phosphoric acid, sulfuric acid, nitric acid, nitrous acid, acetic acid, formic acid, (meth) acrylic acid, oxalic acid and phthalic acid. The lubricant is a residual lubricant which did not participate in the formation of a lubricant layer in the lubrication process. Accordingly, the fluorine-based solution as used herein usually means a used lubricant solution. Of course, depending on the case, the fluorine-based solution may be a solution before a lubricant is added thereto, namely, a fluorine-based solvent exclusively consisting only of a fluorocarbon-based solvent, or may be a fluorine-based solution containing no or only a small amount of residual lubricant. In the former case, the fluorine-based solution means a solution which is preferably purified because impurities are intermixed into the fluorine-based solvent purchased as a raw material for some reason. In the latter case, the fluorine-based solution means a solution which is preferably further purified, though the lubricant is already removed from the used fluorine-based solution in the precedent purification step.

The lubricant in the fluorine-based solution is not particularly limited, however, it is usually a fluororesin having an organic group at the terminal of the structure thereof. This is because, even in the case where a lubricant is present in the fluorine-based solvent, when the lubricant has an organic group at the terminal of the structure, the organic group has polarity and interacts with an adsorbent and therefore, the lubricant is trapped by the adsorbent with good efficiency. The polymer skeleton of the fluororesin is not particularly limited as long as it contains a C–F bond, however, a perfluoroether skeleton is preferred. Accordingly, the fluororesin suitable as the lubricant in the practice of the present invention includes various resins, but a perfluoropolyether resin having at least one polar group at the terminal is preferred. Examples of the polar group of the perfluoropolyether resin include, but are not limited to, an alkyl group (C1 to C20), an alkenyl group, an aryl group, an ether group, an ester group, a hydroxyl group, a sulfonic acid group, a carboxyl group and a piperonyl group. With regard to these polar groups, one polar group may be contained alone or two or more polar groups may be contained in an arbitrary combination. Examples of the perfluoropolyether resin preferred as the lubricant include Fomblin™ AM3001 (Mw=3,200), Fomblin™ AM2001 (Mw=2,400), Fomblin™ Zdol (Mw=2,000) and Fomblin™ Z25 (Mw=9,500) (trade names, all produced by Aujimont).

The fluorocarbon-based solvent used for dissolving the lubricant may be a solvent commonly used for preparing a lubricant solution and is not particularly limited. Examples of the fluorocarbon-based solvent preferred in practice of the present invention include perfluoroalkane compounds and perfluorocycloalkane compounds. These solvents may be used individually or in an arbitrary combination of two or more thereof. Examples of the fluorocarbon-based solvent suitable as the solvent include Fluorinert™ FC-77, Fluorinert™ FC-72, Fluorinert™ FC-84, Fluorinert™ FC-75, Fluorinert™ FC-40, Fluorinert™ FC-43, Fluorinert™ FC-70, Fluoroalkane™ PF50 and Fluoroalkane™ PF5060 (trade names, all produced by Sumitomo 3M).

In the preparation of the fluorine-based solution generally used for forming a lubricant layer, the fluororesin-based lubricant and the fluorocarbon-based solvent, described above, are used by mixing them in different mixing ratios. In general, the fluororesin-based lubricant is used in an amount of about 0.01 to 0.1 wt % based on the entire amount of the fluorine-based solution. After the use for the formation of a lubricant layer, the fluorine-based solution contains a residual fluororesin-based lubricant in an amount of about 0.01 to 0.1 wt % based on the entire amount of the fluorine-based solution. In other words, the content of the residual fluororesin-based lubricant does not greatly fluctuate from the amount before use. This content is a general content empirically known by the present inventor and others and, depending on the case, the content may be smaller or larger than the above-described range. AS described above, the fluorine-based solution of the present invention may not contain a lubricant depending on the case.

The purified fluorine-based solvent of the present invention is obtained after a substantial amount of impurities contained in a trace amount in the fluorine-based solution is selectively removed from the solution by an adsorption process. The term "a substantial amount of impurities is removed" as used herein means that the impurities are removed to the level such that in the measurement by chromatography or the like, impurities of which presence can be distinctly recognized before the purification cannot be detected or, even if the impurities can be detected, the amount is very slight (in the case of ionic impurities, a trace amount of about 5 ng/ml or less) and the obtained solvent can be re-used without causing any problem. In other words, the purified fluorine-based solvent of the present invention have a purity on the order of 99.00% or more.

In the present invention, it is essential to use the adsorption process for removing the impurities. If a conventional purification method such as column chromatography is used, the impurities in an amount larger than the previously expected level cannot be removed from fluorine-based solvent. On the contrary, according to the present invention, the impurities can be, even if each is in a trace amount, effectively trapped by an adsorbent because of the low polarity of fluorine-based solvent and the activity of adsorbent used in the adsorption process, and the impurities once trapped do not again dissolve out into the fluorine-based solvent.

In the practice of the present invention, all of the adsorbent materials well known in this technical field cannot be used with satisfactory results. The present inventors have found that particularly preferred results can be obtained when silica gel or alumina is used as the adsorbent, though the details of the function and effects have not yet been elucidated. These filling agents may be used individually or in combination. Furthermore, if desired, one or more conventional adsorbent, may be additionally used so as to obtain other properties. Of course, the amount of this auxiliary adsorbent is preferably less than about 50%, more preferably less than about 30%, based on the total weight of the adsorbent. Examples of the adsorbent which is confirmed not suitable for the practice of the present invention include Molecular Sieve (trade name, an adsorbent produced by Linde in Germany) and ion exchange resin such as AMBERLITE EG-290-HG (trade name, produced by Rhom and Haas in U.S.A.).

The adsorbent may be used in various shapes but usually is used in the form of powder or small blocks. The size of such an adsorbent is not particularly limited and may be changed over a wide range, however, the size is generally from about 0.05 to 1 mm (as an average diameter).

The adsorbent can be used, as commonly carried out in the adsorption process, by filling a predetermined amount of the adsorbent into a column such as cylindrical column, or a box. However, as long as excellent effects can be attained regarding the trapping of impurities, the adsorbent may be used in a system other than the filling system.

The purified fluorine-based solvent of the present invention has a high capability of containing adsorbent particles derived from the adsorbent used in the adsorption process. The particles have various sizes but the size is usually from about 0.05 to 0.5 mm (as an average diameter). Accordingly, it is preferred to further remove the adsorbent particles from the purified fluorine-based solvent.

The adsorbent particles can be removed using various separation methods. The preferred separation method is, but not limited to, a filtering method (filtration). The filter used in this method may be any type filter as long as it can efficiently remove particles and causes no resoiling, however, a high function filter entirely constructed by perfluororesin (for example, Teflon™ resin) which is widely used, is generally useful. The filtration power of a filter used depends on the pore size of the filter, therefore, a filter having a pore size suitable for the size of particles to be separated by filtration is preferably used. In practice, a fully satisfactory effect of removing particles may be attained by using, for example, a fully Teflon™-made filter having a pore size of about 0.05 μm.

The purified fluorine-based solvent of the present invention can be advantageously used in various ways. For example, this purified solvent can be advantageously used again as a solvent of a fluororesin-based lubricant which is applied to the surface of a functional element such as magnetic disk or magnetic head. Accordingly, the present invention provides not only the purified fluorine-based solvent itself but also a lubricant composition using the solvent. The lubricant composition of the present invention comprises a fluororesin-based lubricant having an organic group at the terminal of the resin structure and a purified fluorine-based solvent as a result of selectively removing ionic pollutants contained in a fluorine-based solution containing a fluorocarbon-based solvent or impurities containing a lubricant from the solution by an adsorption process.

The purified solvent of the present invention can also be advantageously used for cleaning and removing a fluororesin-based lubricant already applied to the surface of a functional element. Accordingly, the present invention also provides a cleaning agent composition using the purified fluorine-based solvent, typically a rinsing solution. The cleaning agent composition of the present invention comprises a fluorocarbon-based solvent, which is used for cleaning a functional element having on the surface thereof a lubricant layer, wherein the fluorocarbon-based solvent is obtained as a result of selectively removing impurities containing ionic pollutants, contained in a fluorine-based solution containing the fluorocarbon-based solvent, and a lubricant from the solution by an adsorption process.

In addition to the above-described purified fluorine-based solvent and a lubricant composition and a cleaning agent composition each using the purified fluorine-based solvent, the present invention provides a method and an apparatus for preparing a purified fluorine-based solvent. That is, the purified fluorine-based solvent of the present invention can be prepared according to various methods, however, is preferably prepared using an adsorption step of selectively removing impurities, containing ionic pollutants contained in a fluorine-based solution, and a lubricant by an adsorption process. As understood from the foregoing description, the adsorption step is preferably performed such that the fluorine-based solution is led to an adsorbent comprising silica gel, alumina or a mixture thereof and impurities are selectively trapped by the adsorbent. It is also preferred, subsequently to the adsorption step, to further perform a filtration step of removing undesirable adsorbent particles intermixed into the fluorine-based solvent in the adsorption step, through a filter.

Figure 1:
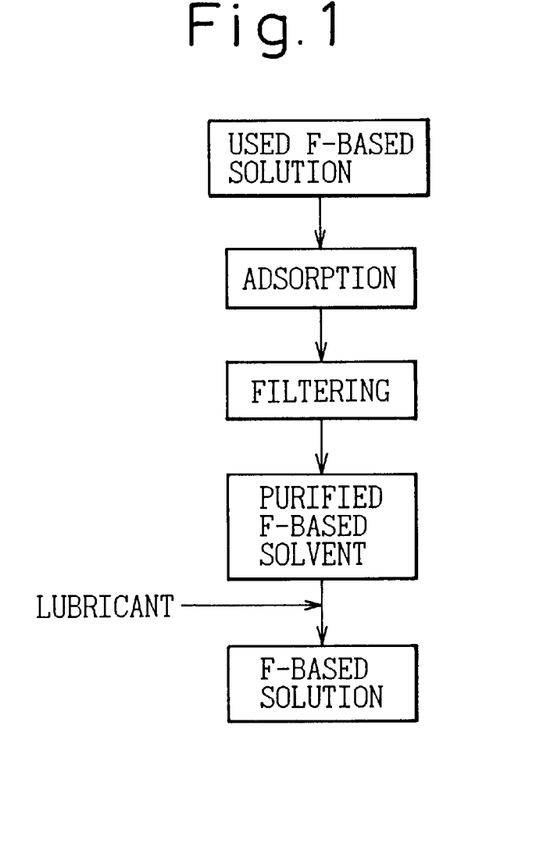
FIG. 1 is a flow sheet explaining the preparation step of the purified fluorine-based solvent according to the present invention.

FIG. 1 is a flow sheet explaining the preparation step of a purified fluorine-based solvent and the subsequent preparation step of a fluorine-based solution according to the present invention. Note in this figure that fluorine is briefly referred to as "F".

More specifically, the preparation of a purified fluorine-based solvent starts from a used fluorine(F)-based solution. As described above, this used fluorine-based solution comprises a fluorine-based solvent, particularly a fluorocarbon-based solvent, and contains trace impurities (foreign matters) such as ionic pollutants and lubricant. The impurities, if not removed, adversely affect or may adversely affect the properties of a functional element such as magnetic disk or properties and operation of a device, having mounted thereon the element, when a lubricant is dissolved in the fluorine-based solvent and applied to the surface of the functional element.

The used fluorine(F)-based solution is treated in an adsorption step to trap the impurities, contained in the solution, by an adsorbent. For the adsorbent, as described above, silica gel, alumina and the like are useful. This adsorbent is used by filling it, for example, into a cylindrical column. The adsorption step can be performed in various treatment forms, however, in general, the step is preferably performed by passing the fluorine-based solution on an adsorbent and also through the inside thereof. In this case, as the flow rate of the fluorine-based solution is lower, the effect of trapping impurities can be higher, however, on taking account of practicability, the preferred flow rate is usually from about 1 to 100 ml/min. The effect of trapping impurities is affected by the ambient temperature and therefore, the adsorption step is usually performed preferably in the vicinity of room temperature (about 25° C.). If the temperature in the adsorption step is excessively low, the viscosity of the fluorine-based solution increases, whereas if the temperature is too high, evaporation of the solution will be accelerated.

In the case of an ordinary fluorine-based solution, impurities in the solution can be almost completely removed by the above-described adsorption step and thus a purified fluorine-based solvent can be obtained. However, depending on the case, particles (powders) derived from the adsorbent used in the adsorption step may be intermixed in the purified fluorine-based solvent. The adsorbent particles also have a possibility of adversely affecting the functional element or properties and operation of a device having mounted thereon the functional element, therefore, as shown in the FIG. 1, a filtration step (a separation step by filtering) is preferably performed following the adsorption step. As described above, the filteration step can be advantageously performed using a fully Teflon™-made filter or others.

Upon completion of the adsorption step and the arbitrary filtration step, a highly purified fluorine(F)-based solvent can be obtained. This solvent already has high purity, therefore, can be used by itself as a fluorine-based solvent or as a rinsing solution in various fields. Furthermore, as shown in the FIG. 1, a predetermined amount of a lubricant may be added thereto to use the solvent for the preparation of a fluorine(F)-based solution.

Figure 2:
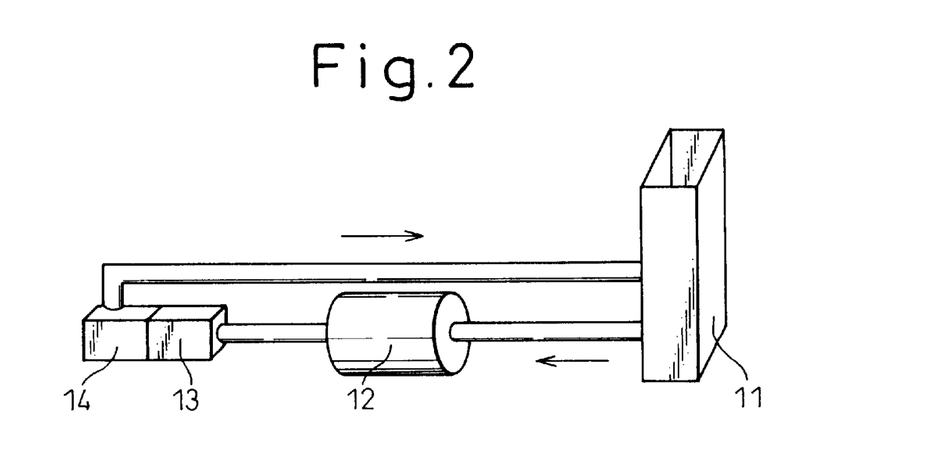
FIG. 2 is a schematic view explaining the apparatus for preparing the purified fluorine-based solvent according to the present invention.

FIG. 2 is a schematic view showing one example of the apparatus for preparing a purified fluorine-based solvent according to the present invention and corresponds to the flow sheet of FIG. 1 referred to and described above. The used fluorine-based solution is contained in a reservoir 11. The reservoir 11 shown is used for applying a lubricant layer to the surface of a magnetic disk as a functional element and is accordingly, designed such that a magnetic disk (not shown) is dipped and pulled up. The fluorine-based solution (now on use) in the reservoir 11 is transferred to an adsorbing station 13 connected through a conduit by means of a pump 12 disposed in the middle on the way. The moving direction of the fluorine-based solution within the conduit is shown by arrows. The adsorbing station 13 is used for trapping various impurities and recovering a purified fluorine-based solvent, and is filled with an adsorbent (e.g., silica gel or alumina) having a predetermined size. In the example shown, a filtering station 14 is provided in the after-stage of the adsorbing station 13 so as to remove adsorbent particles intermixed into the purified fluorine-based solvent. The filtering station 14 is formed of a fully Teflon™-made filter and the fluorine-based solvent passed therethrough is a highly purified fluorine-based solvent. The apparatus shown is constructed to guide this fluorine-based solvent again to the reservoir 11 through a conduit. In other words, this apparatus can be advantageously used as a circulation-type magnetic disk rinsing apparatus, provided with a mechanism of elevating the solvent purity, for continuously rinsing the surface of a magnetic disk on which a lubricant layer is already formed. As is easily understood, a mechanism for recovering the highly purified fluorine-based solvent may also be disposed downstream the filtering station 14. Further, when an exclusive reservoir for recovering the highly purified fluorine-based solvent is provided downstream the filtering station 14 in place of the conduit communicating with the reservoir 11, an apparatus for preparing a purified fluorine-based solvent can be obtained. Furthermore, an apparatus for preparing a fluorine-based solution containing a lubricant can be obtained by further providing a mechanism for adding a predetermined amount of a lubricant.

The present invention provides a functional element having a lubricant layer derived from a fluororesin-based lubricant as an outermost layer, such as magnetic disk and magnetic head. In these functional elements, the purified fluorine-based solvent of the present invention is used for forming the lubricant layer. More specifically, the lubricant layer is formed by coating a fluorine-based solution containing a fluororesin-based lubricant having an organic terminal group and a fluorocarbon-based solvent which is purified according to the present invention and from which impurities intermixed before the purification are selectively removed by an adsorption process.

In the functional element of the present invention, the lubricant layer as an outermost layer may be cleaned with a purified fluorocarbon-based solvent resulting from selectively removing a substantial amount of impurities, intermixed before the purification, by an adsorption process according to the present invention.

As described above, the functional element of the present invention includes various functional mediums and functional members, but a magnetic disk having a lubricant layer as an outermost layer is described below by referring to FIG. 3.

Figure 3:
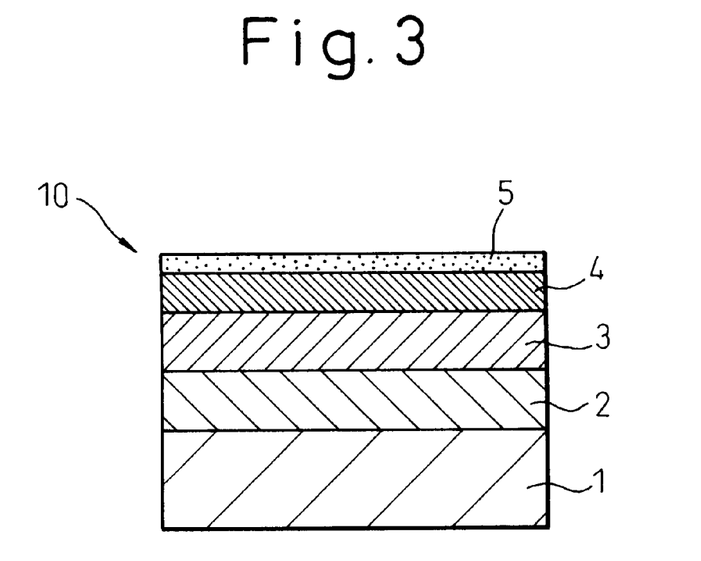
FIG. 3 is a cross-sectional view schematically showing a typical example of the magnetic disk of the present invention.

FIG. 3 is a cross-sectional view schematically showing a layer structure (fundamental structure) of a magnetic disk in general. The magnetic disk 10 comprises, from the bottom, a nonmagnetic substrate 1, a magnetic recording layer (sometimes also referred to as a "magnetic layer") 3, a protective layer 4 and a lubricant layer 5. In this magnetic disk 10, the substrate 1 comprises, for example, an aluminum substrate having adhered, by plating to the surface thereof, an NiP film. The surface is further super-finished. The super finishing is performed to smooth the surface of the substrate 1. The underlayer 2 usually comprises a Cr-based alloy which is a nonmagnetic metal. Examples of the Cr-based alloy include CrMo alloy. The magnetic recording layer 3 usually comprises a CoCr-based alloy which is a ferromagnetic metal. Examples of the CoCr-based alloy include CoCrTa, CoCrPt and CoCrPtTaNb. On this magnetic recording layer 3, a protective layer 4 is provided for protecting the magnetic recording layer from breakage due to impact of the magnetic head. The protective layer 4 is formed from various carbonaceous materials such as amorphous carbon. The protective layer 4 is usually called a carbon protective layer. On the carbon protective layer 4, a liquid lubricant is impregnated to form a lubricant layer 5 so as to attain smooth floating of the head above the magnetic disk 10. As described above, the lubricant is preferably a fluororesin having an organic group at the terminal of the resin structure, for example, perfluoropolyether resin. The layer structure shown is a fundamental structure and the layer structure is actually very complicated.

More specifically, in the magnetic disk shown, the nonmagnetic substrate can be formed from various materials conventionally used in this technical field. Suitable examples of the nonmagnetic substrate include, but are not limited to, NiP-plated aluminum (including aluminum alloy) substrate, glass or tempered glass substrate, silicon substrate having surface oxide film (for example, silicon oxide film), SiC substrate, carbon substrate, plastic substrate and ceramic substrate. Among these, a NiP-plated aluminum (including aluminum alloy) substrate can be advantageously used.

The underlayer on the nonmagnetic substrate can be formed from a nonmagnetic metal material commonly used for conventional magnetic disks, preferably from a nonmagnetic metal material mainly comprising chromium. The underlayer may have a single layer structure or a multilayer structure comprising two or more layers. In the case of an underlayer having a multilayer structure, the composition of each layer may be freely changed. In particular, the underlayer is advantageously constructed by a metal material mainly comprising only chromium or a metal material mainly comprising chromium and molybdenum. For example, in the case where the magnetic recording layer of the magnetic disk contains platinum, the underlayer is preferably constructed by a metal material mainly comprising chromium and molybdenum. Suitable examples of the material for the underlayer include Cr, CrW, CrV, CrTi and CrMo. The underlayer is preferably formed by a sputtering process such as magnetron sputtering, under general film-forming conditions. If desired, other film-forming methods such as vapor deposition and ion beam sputtering, may be used in place of the sputtering. The thickness of the underlayer can be varied over a wide range according to various factors. In order to increase the S/N ratio, the thickness of the underlayer is generally from 5 to 60 nm, however, the thickness of the underlayer is not limited to this range.

In the magnetic disk, an additional underlayer comprising a metal material containing titanium as a main component, preferably a Ti thin film, may be provided between the nonmagnetic substrate and the underlayer above the substrate, if desired. This intermediate layer has a function of more improving the bonding strength between the substrate and the underlayer.

In the magnetic disk, the magnetic recording layer formed on the nonmagnetic underlayer can be formed, similarly to the underlayer, of a general magnetic recording layer commonly used in magnetic recording mediums. The magnetic recording layer may have a single layer structure or a multilayer structure comprising two or more layers. In the case of a magnetic recording layer having a multilayer structure, the compositions of respective magnetic recording layers may be the same or different and if desired, an intermediate layer may be interposed between magnetic recording layers to improve the magnetic recording properties.

For example, the magnetic recording layer may be constructed by, in the case of a single layer structure, a five-element-based alloy mainly comprising cobalt and containing:

| | |
|---|---|
| Chrome | 14 to 23 at %, and |
| Platinum | 1 to 20 at %, | and by further combining therewith tungsten and carbon.

In the case where the magnetic recording layer of the magnetic recording medium has a two-layer structure, the upper magnetic recording layer can employ the above-described magnetic recording layer comprising a CoCrPtWC five-element-based alloy. For the under magnetic recording layer disposed in the middle between the upper magnetic recording layer and the underlayer, a magnetic recording layer constructed by a five-element-based alloy mainly comprising cobalt and containing:

| | |
|---|---|
| Chrome | 13 to 21 at %, and |
| Platinum | 1 to 20 at %, | and by further combining therewith tantalum and niobium may be used.

In the magnetic disk, irrespective of a single layer structure or a two-layer structure, the magnetic recording layer preferably has a tBr (a product of the thickness t of magnetic recording layer and the remnant magnetization density Br) of about 30 to 180 G$\mu$m. In particular, the magnetic recording layer having a single layer structure preferably has a tBr of about 50 to 180 G$\mu$m and the magnetic recording layer having a two-layer structure preferably has a tBr of about 30 to 160 G$\mu$m. Thus, the magnetic recording layer is constructed to have a low Br as compared with conventional magnetic recording layers and therefore, is optimal for use in the magneto-resistance effect type heads including MR head.

The magnetic recording layer provided through an underlayer on a nonmagnetic substrate is, as described above, preferably constructed by a CoCrPtWC five-elemen-based alloy or, if desired, constructed by an upper layer comprising a CoCrPtWC five-element alloy and a lower layer comprising a CoCrPtTaNb five-element alloy. The magnetic recording layer is preferably formed using, for example, magnetron sputtering. If desired, other film-forming methods such as vapor deposition and ion beam sputtering may be used.

The magnetic disk comprises a carbon protective layer on the magnetic recording layer for protecting the magnetic recording layer. The carbon protective layer may be formed by a sputtering method or a chemical vapor deposition method (CVD method), which are film-forming techniques commonly used in the production of semiconductor devices. Furthermore, in order to impart improved durability to the thus-formed carbon protective layer, hydrogen or nitrogen may be added to the carbon protective layer. Examples of the reinforced carbon protective layer include hydrogenated carbon protective film. In place of the sputtering method or CVD method, the carbon protective layer may be formed by a filtered cathodic arc method (FCA) which is a technique developed in recent years. According to this method, a carbon protective layer having high hardness accumulates on the magnetic recording layer and at the same time, when nitrogen is incorporated into the carbon protective layer having high hardness, the carbon protective layer is greatly improved in the adsorptivity to a liquid lubricant, whereby excellent durability can be obtained and maintained. The carbon protective layer may be variously changed in the thickness as generally used in magnetic disks.

On the carbon protective layer, a lubricant layer comprising a perfluoroether resin is preferably formed according to the present invention. This is already described above. The lubricant layer has a function of, as described above, preventing a hindrance called a head crash destroying the magnetic recording data due to contact of the head with the medium and moreover, reducing the frictional force accompanying the sliding between the head and the medium, and thereby prolonging the life of the medium. The thickness of the lubricant layer is usually from about 0.5 to 3 nm.

Although not shown, the carbon protective layer can be advantageously applied also to the magnetic head, because the magnetic head can fundamentally have the same layer structure as that of the magnetic disk.

With regard to the magnetic head, with the progress of information processing technology in recent years, higher density is increasingly demanded for a magnetic disk device used in the external memory unit of a computer and on considering this tendency, a magneto-resistance effect type head using a magneto-resistive element capable of causing change in the electric resistance according to the intensity of the magnetic field, namely, MR head, is preferably used instead of conventional wound-rotor inductive thin film magnetic heads. The MR head applies the magneto-resistance effect such that the electric resistance of the magnetic substance is changed by the external magnetic field, to the reproduction of signals on the recording medium and is characterized in that the reproduction output width is as large as several times the width of conventional inductive thin film magnetic heads, the inductance is small and the S/N ratio is large. In addition to this MR head, an AMR head using an anisotropic magneto-resistance effect, a GMR head using a giant magneto-resistance effect and as a practical type thereof, a spin valve GMR head may also be preferably used.

EXAMPLES

The present invention will be described below by referring to the Examples. These Examples are only one example and it should be understood that the present invention is not limited to these Examples.

Example 1

Preparation of Purified Fluorine-Based Solvent

A glass tube having a diameter of 2.5 cm and a length of 30 cm was prepared and after filling of about 100 g of silica gel powder (average particle size: about 0.5 mm) as an adsorbent, fixed to a stand to lie vertically. A perfluoropolyether resin, Fomblin™ AM3001 (trade name, Mw: 3,200) produced by Aujimont was selected as the lubricant and this was dissolved in a fluorocarbon-based solvent, Fluorinert™ FC-77 (trade name) produced by Sumitomo 3M to have a lubricant content of 0.02 wt %. The amounts of impurities contained in the obtained lubricant solution were analyzed by ion chromatography, as a result, the solution was confirmed to contain various impurities each in a slight amount as shown in Table 1 below. For the analysis by ion chromatography, an analyzer "DX-500" (trade name) manufactured by Dionex was used.

The thus-prepared lubricant solution was continuously passed through the silica gel column manufactured above from the top thereof. The amount of the lubricant solution passed was about 1 kg in total and the passing rate (flow rate) was about 10 ml/min. A clear solution (purified fluorocarbon-based solvent) was recovered in a receiver disposed at the lower end of the silica gel column and the amounts of impurities contained in the solution were again analyzed according to the same procedure as above by ion chromatography. As a result, as shown in Table 1 below, it was confirmed that substantially all of the impurities contained in the initial lubricant solution were removed during the passage through the silica gel column.

Subsequently, the recovered solution was measured in the ultraviolet absorption spectrum to examine whether or not lubricant was contained in the solution recovered in the receiver. From the measurement results, the solution was confirmed not to contain lubricant even in a trace amount, in other words, the lubricant was completely trapped by the silica gel filled in the column. Also, from the calculation based on the absorbency at 270 nm, the concentration of the lubricant was confirmed to be 0 wt %.

Example 2

Preparation of Purified Fluorine-Based Solvent

The procedure of Example 1 was repeated except that in this Example, alumina powder (average particle size: about 0.1 mm) was used as the adsorbent filled in the column in place of silica gel powder. The same lubricant solution as used in Example 1 was continuously passed through the alumina column and the amounts of impurities contained in the solution recovered in the receiver were analyzed by ion chromatography. As shown in Table 1 below, it was confirmed that substantially all of impurities contained in the initial lubricant solution were removed during the passing through the alumina column.

Subsequently, the recovered solution was measured on the ultraviolet absorption spectrum to examine whether or not the lubricant was contained in the solution recovered in the receiver. From the measurement results, the solution was confirmed not to contain the lubricant even in a trace amount, in other words, the lubricant was completely trapped by the alumina filled in the column.

TABLE 1

| Impurities in Lubricant Solution | Concentration* Before Purification | Concentration* in Recovered Solution | |
|---|---|---|---|
| | | Example 1 | Example 2 |
| Fluorine | 0.02 | 0.00 | 0.00 |
| Bromine | 0.00 | 0.00 | 0.00 |
| Chlorine | 0.15 | 0.08 | 0.02 |
| Phosphoric acid | 0.00 | 0.00 | 0.00 |
| Sulfuric acid | 0.00 | 0.02 | 0.00 |
| Nitric acid | 0.36 | 0.05 | 0.00 |
| Nitrous acid | 0.41 | 0.26 | 0.05 |
| Acetic acid | 0.39 | 0.47 | 0.08 |
| Formic acid | 2.38 | 0.26 | 0.00 |
| Methacrylic acid | 0.00 | 0.00 | 0.00 |
| Oxalic acid | 0.00 | 0.00 | 0.00 |
| Phthalic acid | 0.00 | 0.00 | 0.00 |
| | 3.71 | 1.13 | 0.14 |

(Concentration*: ng/ml, by ion chromatography)

As seen from the results in Table 1, when a fluorine-based solution is purified using silica gel or alumina as the adsorbent according to the present invention, trace impurities contained can be very effectively removed.

Comparative Example 1

Preparation of Purified Fluorine-Based Solvent

The procedure of Example 1 was repeated except that in this Example, Molecular Sieves (average particle size: about 0.1 mm) was used as the adsorbent filled in the column in place of silica gel powder. A perfluoropolyether resin, Fomblin™ AM3001 (trade name, Mw: 3,200) produced by Aujimont was selected as the lubricant and this was dissolved in a fluorocarbon-based solvent, Fluorinert™ FC-77 (trade name) produced by Sumitomo 3M to have a lubricant content of 0.02 wt %. The amounts of impurities contained in the obtained lubricant solution were analyzed by ion chromatography in the same manner as in Example 1, as a result, the solution was confirmed to contain various impurities each in a slight amount as shown in Table 2 below. The amounts of impurities contained in the lubricant solution used in this Example were not the same as those in Table 1 and this occurred because the lubricant and the fluorocarbon-based solvent were taken out from different batches.

The thus-prepared lubricant solution was continuously passed through the Molecular Sieves column and the amounts of impurities contained in the solution recovered in the receiver were analyzed by ion chromatography. As shown in Table 2 below, the impurities contained in the initial lubricant solution could not be completely removed but rather the amounts of impurities considered to be derived from the Molecular Sieves were outstandingly increased.

Subsequently, the recovered solution was measured in the ultraviolet absorption spectrum to examine whether or not the lubricant was contained in the solution recovered in the receiver. From the measurement results, it was confirmed that the lubricant not adsorbed to the Molecular Sieves was present in the solution in a recognizable amount.

TABLE 2

| Impurities in Lubricant Solution | Concentration* Before Purification | Concentration* in Recovered Solution |
|---|---|---|
| Fluorine | 0.04 | 0.80 |
| Bromine | 0.00 | 0.00 |
| Chlorine | 0.16 | 0.36 |
| Phosphoric acid | 0.00 | 32.88 |
| Sulfuric acid | 0.13 | 9.65 |
| Nitric acid | 0.36 | 0.07 |
| Nitrous acid | 0.11 | 0.47 |
| Acetic acid | 2.22 | 1.18 |
| Formic acid | 1.89 | 0.52 |
| Methacrylic acid | 0.00 | 0.00 |
| Oxalic acid | 0.00 | 0.00 |
| Phthalic acid | 0.00 | 0.00 |
| | 4.91 | 45.94 |

(concentration*: ng/ml, by ion chromatography)

As seen from the results shown in Table 2, when a fluorine-based solvent was purified using Molecular Sieves as the adsorbent, the contents of impurities were rather increased and this reveals that the selection of adsorbent is important.

Example 3

Preparation of Lubricant Solution 1

A purified fluorine-based solvent was prepared according to the procedure described in Example 1. A fluorocarbon-based solvent, Fluorinert™ FC-77 (trade name) produced by Sumitomo 3M was passed through the silica gel column manufactured in Example 1 to adsorb the impurities contained in the solvent to silica gel.

Subsequently, in order to remove silica gel particles having a diameter of 0.01 μm or more considered to be intermixed in the solvent after the purification, the purified solvent recovered at the lower end of the silica gel column was further passed through a fully Teflon™-made filter having a pore size of 0.05 μm.

A perfluoropolyether resin, Fomblin™ AM3001 (trade name, Mw: 3,200) produced by Aujimont was selected as the lubricant and this was dissolved in the solvent purified as above to have a lubricant content of 0.02 wt %. The thus-obtained lubricant solution was designated as "Lubricant Solution 1".

Example 4

Preparation of Lubricant Solution 2

A purified fluorine-based solvent was prepared according to the procedure described in Example 1. A fluorocarbon-based solvent, Fluorinert™ FC-77 (trade name) produced by Sumitomo 3M was passed through the alumina column manufactured in Example 2 to adsorb the impurities contained in the solvent to alumina. Subsequently, in order to remove alumina particles having a diameter of 0.01 μm or more considered to be intermixed in the solvent after the purification, the purified solvent recovered at the lower end of the alumina column was further passed through a fully Teflon™-made filter having a pore size of 0.05 μm.

A perfluoropolyether resin, Fomblin™ AM3001 (trade name, Mw: 3,200) produced by Aujimont was selected as the lubricant and this was dissolved in the solvent purified as above to have a lubricant content of 0.02 wt %. The thus-obtained lubricant solution was designated as "Lubricant Solution 2".

Example 5

Manufacture of Magnetic Disk

A magnetic disk having the following layer structure was manufactured.

Lubricant Layer
Nitrogen-Doped Carbon Protective layer
Magnetic Recording Layer (CoCrPtTaNb)
Underlayer ($CrMo_{10}$)
NiP-Plated Aluminum Substrate NiP was plated on an aluminum (Al) substrate to form a NiP-plated layer and thereafter, the surface was well washed and then thoroughly smoothened by a texturing treatment. On the thus-obtained NiP/Al substrate, a CrMo10 (at%) underlayer, a CoCrPtTaNb-system magnetic recording layer, a nitrogen-doped carbon (C) protective layer and a lubricant layer comprising "Fomblin™ AM3001" (trade name) were sequentially deposited according to the following procedure using a DC magnetron sputtering apparatus.

Before the formation of underlayer, the sputtering chamber was evacuated to $3\times10^{-7}$ Torr or less, the substrate temperature was elevated to 280° C., and the sputtering chamber was kept at 5 mTorr by introducing an Ar gas. While applying a bias voltage of −200 V, CrMo as the underlayer was deposited at a thickness of 30 nm. After the formation of underlayer, the CoCrPtTaNb film was formed to have a Brt of 100 Gμm (thickness of 27 nm). The target used for the film formation was a composite target obtained by disposing Pt, Ta and Nb chips to a CoCr target. Thereafter, a nitrogen-containing carbon protective layer was deposited at a thickness of 5 nm using an FCA film-forming apparatus under the following film forming conditions.

Arc current: 80 A
Cathode coil current: 10 A
Filter coil current: 10 A, 6 A
Luster coil current:X: 0 A, Y: 10 A After the formation of the carbon protective layer, Lubricant Solution 1 prepared in Example 3 was coated on the surface of the carbon protective layer by a dip coating method to a thickness of 2.5 nm and then dried.

As a result, a magnetic disk having the above-described layer structure was obtained.

[Test of Properties]

The magnetic disk manufactured above was mounted on a magnetic disk device provided with a thin MR head, "MPF3102AT" (trade name) manufactured by Fujitsu, and subjected to a cycle test consisting of operation for 15 seconds at a rotation speed of 5,400 rpm and stopping for 15 seconds, and the CSS properties were measured by a disk abrasion tester. As a result, even after the cycle test was repeated 10,000 times, abrasion of a recognizable level was not generated on the magnetic disk surface and the MR head maintained good state. This magnetic disk was then subjected to a normal drive evaluation in the same magnetic disk device, but no abnormality was found.

Subsequently, another magnetic disk was manufactured in the same manner as above except for using Lubricant Solution 2 prepared in Example 4 in place of Lubricant Solution 1. This magnetic disk was tested on the properties in the same manner as above, as a result, good results comparable to the results in the test above could be obtained.

Example 6

Rinsing Treatment of Magnetic Disk

A magnetic disk was manufactured in the same manner as in Example 5 and then subjected to a rinsing treatment using a purified fluorine-based solvent so as to remove extra lubricant adhering to the surface of the magnetic disk. For this rinsing treatment, a circulation-type rinsing apparatus described above by referring to FIG. 2 was used.

In a reservoir 11 having an opened upper surface, a fluorocarbon-based solvent, Fluorinert™ FC-77 (trade name) produced by Sumitomo 3M was housed to a predetermined level. Thereafter, the solvent in the reservoir 11 was transferred to an adsorbing station 13 by means of a pump 12. In the adsorbing station 13, silica gel powder having an average particle size of 0.1 μm was filled as an adsorbent, therefore, during the solvent passing through the inside thereof, trace impurities intermixed in the solvent were trapped by the silica gel. After the separation of impurities, the solvent was guided into a filtering station 14 disposed in the after-stage of the adsorbing station 13. In the filtering station 14, a fully Teflon™-made filter having a pore size of 0.05 μm was fixed and therefore, silica gel particles (having a diameter of 0.01 μm or more) intermixed in the solvent could be removed through the filter. The thus completely purified solvent was returned to the reservoir 11.

While circulating the fluorine-based solvent purified above within the rinsing apparatus, an operation of dipping 500 sheets in total of magnetic disks one by one in the reservoir 11 and pulling it up, thereby performing rinsing was repeated. For each rinsing, the extra lubricant adhering to the magnetic disk surface could be removed and a magnetic disk comprising a lubricant layer having a thin and uniform thickness could be obtained. In this rinsing treatment, whether or not the lubricant dissolved out due to the rinsing treatment or trace impurities were intermixed in the fluorine-based solvent immediately before returning to the reservoir 11 was measured by ion chromatography and an ultraviolet absorption spectrum method and, as a result, it was confirmed that the solvent had high purity on the same level as that of the purified solvent initially housed in the reservoir 11.

Subsequently, the above-described rinsing treatment was repeated by filling alumina powder (average particle size: about 0.1 mm) as the adsorbent to the adsorbing station 13 in place of the silica gel powder. The results obtained were comparable to the results above and thus satisfactory.

Finally, for the purpose of comparison, an operation of dipping a magnetic disk in a fluorine-based solvent of a non-circulation system rinsing apparatus (reservoir 11) not equipped with an adsorbing station and a filtering station, and pulling it out was repeated, as a result, from the rinsing of about 30th magnetic disk, the thickness of the lubricant layer was liable to be non-uniform.

In addition, it was verified that when such a magnetic disk having a non-uniform lubricant layer is used in a magnetic disk device, the flying property of the MR head deteriorates.

As described in the foregoing pages, according to the present invention, a lubricant composition can be provided, which is useful for the formation of a lubricant layer on the surface of a functional element such as magnetic disk, contains only a negligible amount of pollutants having an adverse effect on the surrounding environment, is inexpensive, and can be easily recycled.

Also, according to the present invention, a highly purified fluorine-based solvent useful for the preparation of the above-described lubricant composition; a production process and a production apparatus therefor; and a cleaning agent composition using the fluorine-based solvent, can be provided.

Furthermore, according to the present invention, a fluorine-based solvent recycling system capable of remarkably reducing the concentration of pollutants contained can be provided.

Still further, according to the present invention, a magnetic disk or other functional elements having on the surface thereof an excellent lubricant layer and favored with high quality and low cost can be provided by using the above-described lubricant composition or cleaning agent composition.

What is claimed is:

1. A method for preparing a purified fluorine-based solvent from a used fluorine-based solution comprising a fluorocarbon-based solvent along with a trace amount of ionic organic impurities and a residual lubricant based on a fluororesin having an organic terminal group, comprising an adsorption step of selectively removing the impurities and the residual lubricant by an adsorption process.

2. The method for preparing a purified fluorine-based solvent as recited in claim 1, wherein the fluororesin as the lubricant is a perfluoropolyether resin having at least one polar group at the terminal thereof.

3. The method for preparing a purified fluorine-based solvent as recited in claim 2, wherein the polar group of the perfluoropolyether resin is selected from the group consisting of an ether group, an ester group, a hydroxyl group, a sulfonic acid group, a carboxyl group and a piperonyl group.

4. The method for preparing a purified fluorine-based solvent as recited in claim 1, wherein the fluorocarbon-based solvent is a perfluoroalkane compound or a perfluorocycloalkane compound.

5. The method for preparing a purified fluorine-based solvent as recited in claim 1, wherein in the absorption step, the fluorine-based solution is supplied on the adsorbent comprising silica gel, alumina or a mixture thereof to selectively trap the impurities and the residual lubricant by the adsorbent.

6. The method for preparing a purified fluorine-based solvent as recited in claim 5, which further comprises a filtration step of removing the adsorbent particles incorporated into the fluorine-based solvent during the adsorption step, through a filter.

7. An apparatus for preparing a purified fluorine-based solvent from a fluorine-based solution comprising a fluorocarbon-based solvent along with a trace amount of ionic organic impurities and a residual lubricant based on a fluororesin having an organic terminal group, comprising an adsorbing station filled with an adsorbent capable of trapping the impurities and the residual lubricant, disposed on the way of passage of the fluorine-based solution.

8. The apparatus for preparing a purified fluorine-based solvent as recited in claim 7, wherein in the absorbing station, the adsorbent comprises silica gel, alumina or a mixture thereof.

9. The apparatus for preparing a purified fluorine-based solvent as recited in claim 7 or 8, which further comprises a filtering station for removing adsorbent particles incorporated into the fluorine-based solvent, in the after-stage of the adsorbing station.

* * * * *